United States Patent

Macaluso, Jr.

[11] Patent Number: 5,141,502
[45] Date of Patent: Aug. 25, 1992

[54] URETERAL STENT

[76] Inventor: Joseph N. Macaluso, Jr., #8 English Turn Dr., New Orleans, La. 70131

[21] Appl. No.: 750,969

[22] Filed: Aug. 28, 1991

[51] Int. Cl.⁵ ............................................ A61M 25/00
[52] U.S. Cl. .................................................... 604/281
[58] Field of Search ............... 604/281, 280, 282, 264, 604/54, 8, 164-170

[56] References Cited

U.S. PATENT DOCUMENTS

| | | | |
|---|---|---|---|
| 4,531,933 | 7/1985 | Norton et al. | 604/281 |
| 4,671,795 | 6/1987 | Mulchin | 604/281 |
| 4,790,809 | 12/1988 | Kuntz | 604/280 X |
| 4,813,925 | 3/1989 | Anderson, Jr. et al. | 604/54 X |
| 4,874,360 | 10/1989 | Goldberg et al. | 604/281 X |
| 4,887,996 | 12/1989 | Bengmark | 604/281 X |
| 4,950,228 | 8/1990 | Knapp, Jr. et al. | 604/8 |

Primary Examiner—John D. Yasko
Attorney, Agent, or Firm—Pravel, Gambrell, Hewitt, Kimball & Krieger

[57] ABSTRACT

A ureteral stent includes a stiffer stent body that affords superior columnar and axial strength for smooth advancement during insertion into a patient's ureter, and a softer bladder coil portion for reducing the risk of irritation at the trigone. A collar forms an interface between the stiffer stent body and the softer bladder coil. The collar has an annular shoulder that faces the bladder coil, providing a load transfer surface for controlled placement of the stent with a pusher tube that rides over the bladder coil. A pusher assembly includes a first inner and smaller diameter pusher having the diameter of the bladder coil, and a larger diameter pusher tube having the diameter of the collar anular shoulder. For easier placements, the smaller pusher tube bears against the bladder tube. For more difficult placements, the larger pusher tube can ride over the smaller pusher tube and engage the annular shoulder of the collar. A guide wire fits within the bore of the stent main tube body and the bore of the bladder tube. The guide wire also fits a bore of the smaller pusher tube. The guide defines a path for installation of the stent and for the pushers.

24 Claims, 3 Drawing Sheets

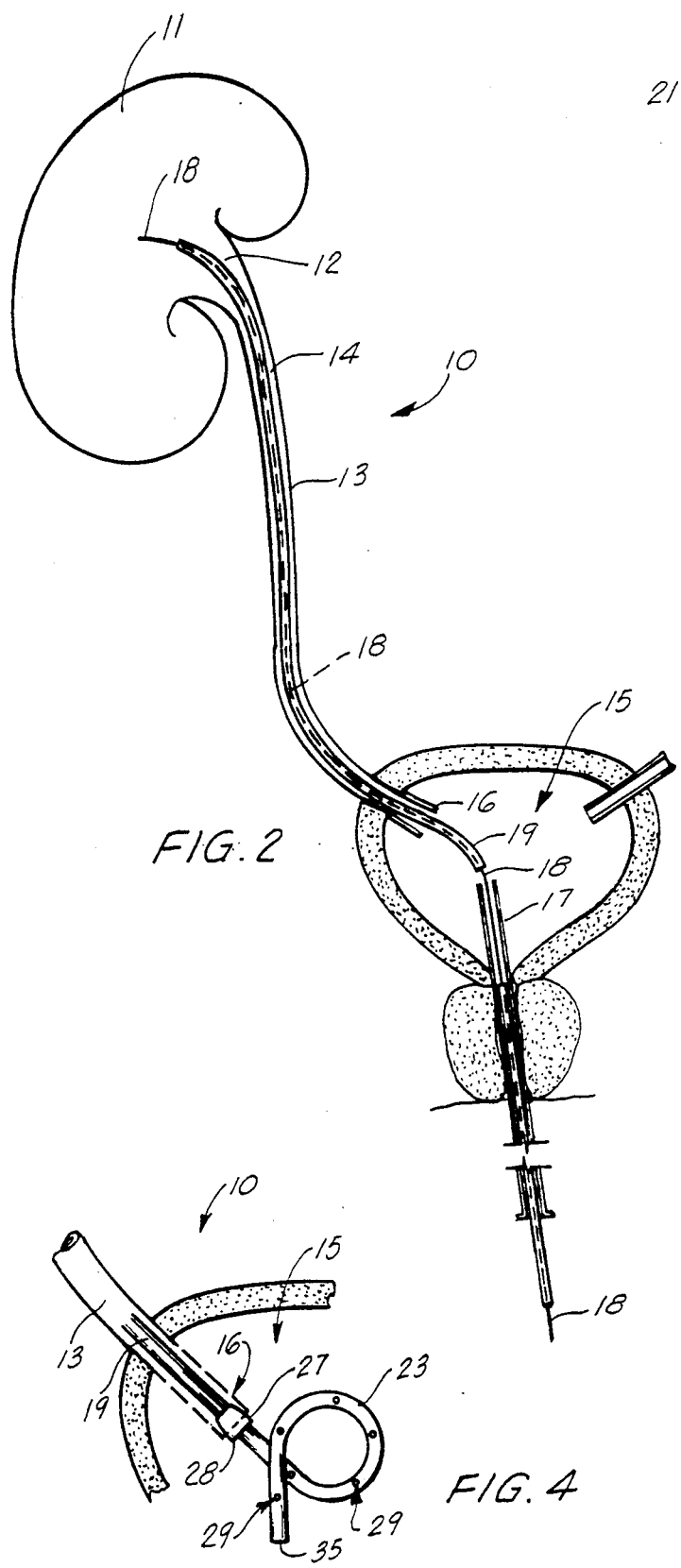
FIG. 2
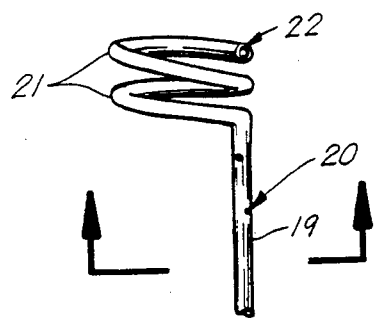
FIG. 5
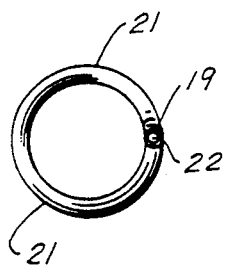
FIG. 6
FIG. 4

URETERAL STENT

BACKGROUND OF THE INVENTION

1. Field of the Invention

The present invention relates to ureteral stents, and more particularly relates to an improved stent for placement in a patient's ureter wherein the stent body is of a stiffer material to promote smooth advancement, and the bladder coil is of a softer material that reduces irritation at the trigone, and a collar interfaces the stent body and bladder coil, the collar having an annular shoulder that accepts a pusher tube above the bladder coil.

2. General Background

Common problems encountered during ureteral stenting include stent buckling during placement, antegrade and retrograde migration, and patient discomfort. Some stents use J-shaped end portions that register in the renal pelvis and bladder respectively. The J-shaped ends can straighten at the top or proximate end portion of the stent so that the entire stent migrates in the ureter.

Most stents are of a singular material. This requires a stent of stiff enough material so that the stent can be installed with a pusher without risk of buckling. However, this stiff stent material can irritate bladder tissue.

SUMMARY OF THE INVENTION

The present invention provides an improved ureteral stent that affords a solution to ureteral stenting problems that includes stent buckling during placement, antegrade migration, and patient discomfort.

The tube body of the stent and the helix kidney coil are constructed of a firm material such as a polymer that is commercially available and sold under the trademark C-FLEX ®. This provides for superior strength for reduced buckling during advancement and stability of position in the renal pelvis.

In contrast, softer material is used for the bladder coil to ensure enhanced patient comfort.

A unique collar at the base of the bladder coil permits efficient, controlled placement of the ureteral stent apparatus. The use of the collar at the base of the bladder coil also permits visual confirmation of stent position in addition to the control of stent placement.

A pusher arrangement rides upon a guide wire for choice of placement techniques, including placement of the stent using the smaller tube, placement of the stent using the larger pusher tube, or a placement that involves both the larger and smaller pusher tubes.

It is thus an object of the present invention to provide an improved ureteral stent apparatus that solves the problems of stent migration by providing a substantially non-migratable stent apparatus, a stent that is easily installed and which eliminates substantially all buckling problems, and further a stent that eliminates patient discomfort relating to the bladder coil area.

The present invention provides an improved ureteral stent apparatus that has an elongated flexible tube body having a bore for carrying fluid therein. The tube body includes a proximal or upper end portion and a distal or lower end portion.

The tube body includes a double helical portion at the proximal end portion of the tube body that is positioned during use at the patient's renal pelvis.

A bladder coil is positioned at the distal end portion of the tube body and with a bore that communicates with the tube body bore.

The tube is preferably of a polymeric material and the bladder coil is also preferably of a polymeric material but is a softer material than the material used in the tube body.

In the preferred embodiment, the apparatus includes a collar that is positioned between the tube body and the bladder coil. The collar also includes a bore that communicates with the bore of the tube body and of the bladder coil so that flow passes between the bladder coil and tube body. The tube body and collar are preferably of a radiopaque material for visual inspection during placement.

In the preferred embodiment the helical structure is in the form of a coil that defines a double helical structure. Further, the double helix is offset laterally with respect to the central axis of the tube body bore. This enhances an anchorage of the proximal end portion of the ureteral stent apparatus in the renal pelvis and eliminates substantial migration problems.

BRIEF DESCRIPTION OF THE DRAWING

For a further understanding of the nature and objects of the present invention, reference should be had to the following detailed description, taken in conjunction with the accompanying drawings, in which like parts are given like reference numerals, and wherein:

FIG. 2 is a schematic illustration of the preferred embodiment of the apparatus of the present invention shown during installation and after placement of the ureteral stent into operative position and prior to removal of the guide wire and cystoscope;

FIG. 3 is a schematic illustration of the preferred embodiment of the apparatus of the present invention shown during installation and prior to the removal of guide wire and pusher tube members;

FIG. 4 is a fragmentary schematic illustration of the preferred embodiment of the apparatus of the present invention after placement of the ureteral stent inoperative position and with the guide wire and pusher tubes removed;

FIG. 5 is a fragmentary view of the preferred embodiment of the apparatus of the present invention;

FIG. 6 is a schematic end view of the ureteral stent of the present invention;

DETAILED DESCRIPTION OF THE PREFERRED EMBODIMENT

Figure 1:
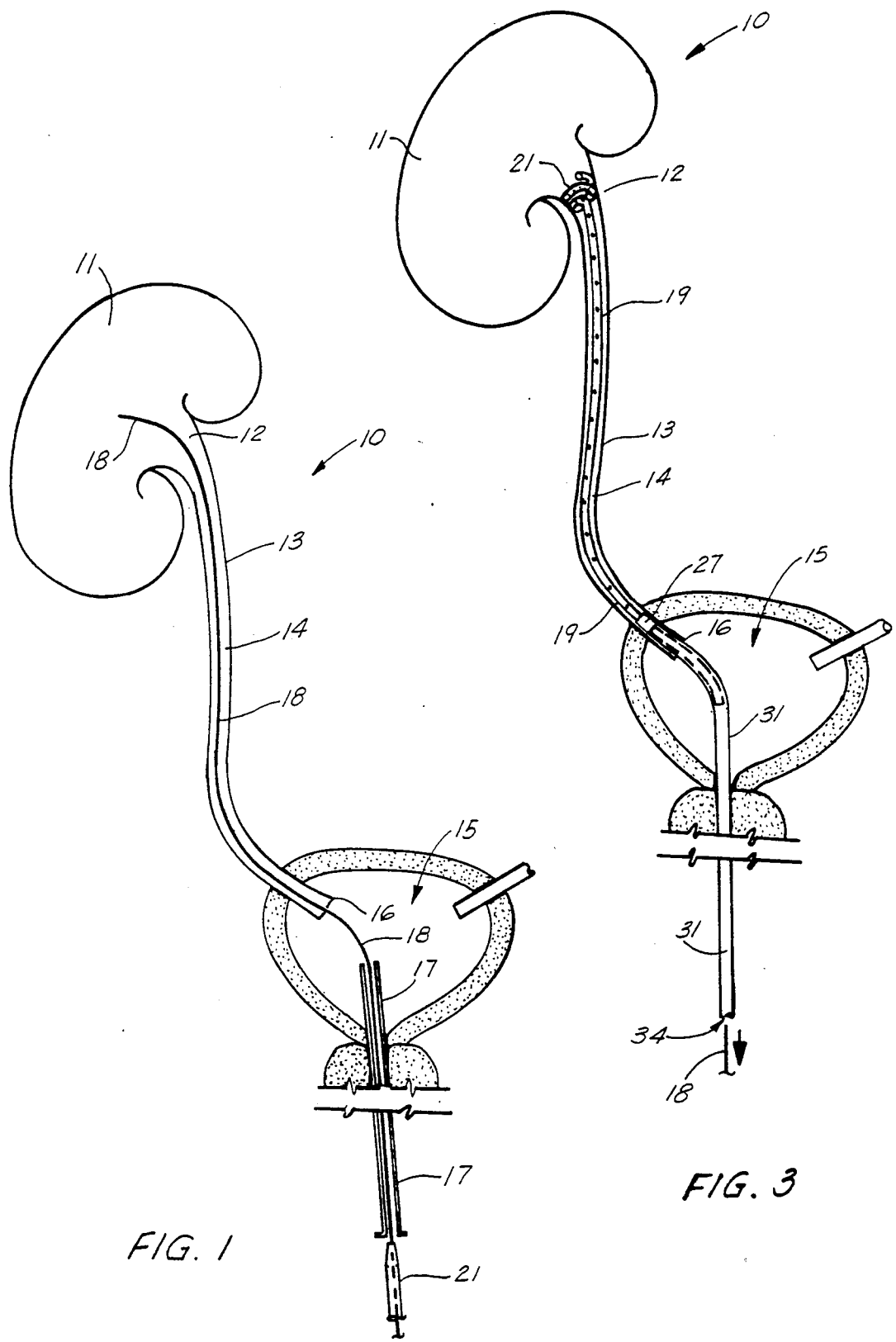
FIG. 1 is a schematic illustration of the apparatus of the present invention illustrating the guide wire portion thereof during installation.

FIGS. 1-4 illustrate installation of the ureteral stent apparatus 10 of the present invention. In FIGS. 1-3, the patient's kidney is designated generally by the numeral 11. The ureter is designated by the numeral 13 and bladder 15 is illustrated. Ureter 13 includes a bore or lumen 14 and the upper portion of ureter 13 is of an expanded or funnel-shaped configuration and is known as the renal pelvis 12. At the lower end of the ureter 13 is the ureteral orifice 16 that extends partially into the bladder 15 as shown in FIGS. 1-4 in the drawings.

Figure 7:
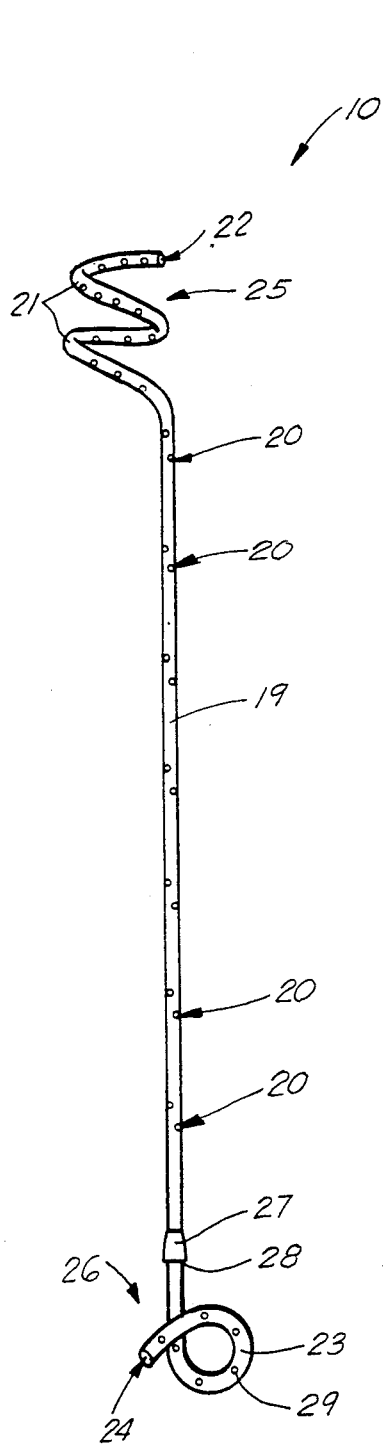
FIG. 7 is an elevational view of the preferred embodiment of the apparatus of the present invention.

During use, the ureteral stent apparatus 10 of the present invention is installed by a physician using an elongated guide wire 18 that extends from the physician's instrument known as a cystoscope 17, through the ureteral orifice 16, and then into the lumen 14 of ureter 13 until the guide wire 18 reaches the patient's renal pelvis 12 and kidney 11, as shown in FIG. 1. In this position, the ureteral stent is just beginning to be threaded onto the guide wire 18. The physician threads the uppermost or proximate end 21 of the ureteral stent 10 onto the guide wire 18. The proximate 21 end portion of the ureteral stent apparatus 10 is a double helix 21 portion, as shown in FIGS. 5 and 7.

After placement of guide wire 18, the physician pushes the ureteral stent tube body 19 upwardly on the wire 18 until the physician no longer is able to grip the lowermost or distal end of the tube body 19. This position is illustrated in FIG. 2 of the drawings.

Figure 8:
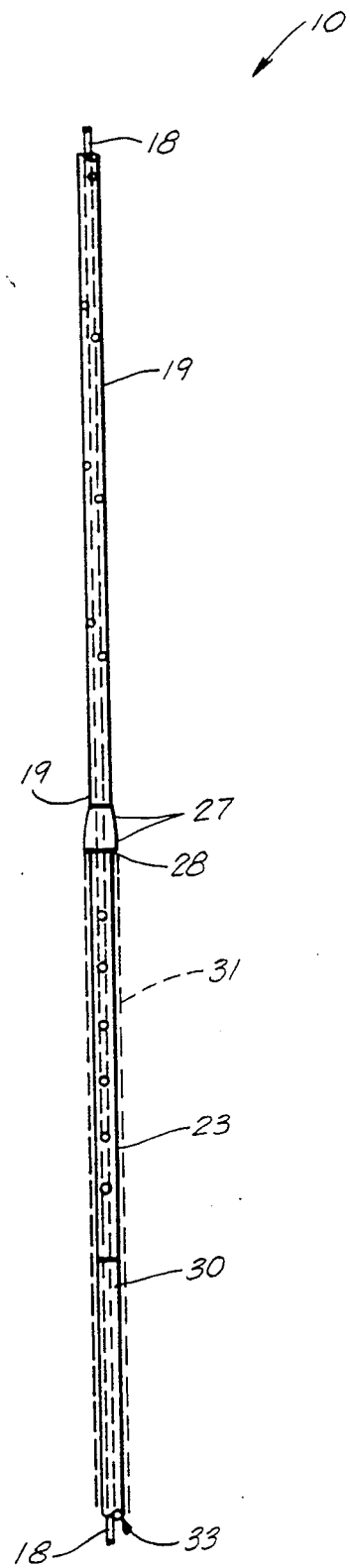
FIG. 8 is a schematic view illustrating installation of the ureteral stent of the present invention using an interior or smaller pusher tube with a second larger diameter pusher tube being shown in phantom lines.
Figure 9:
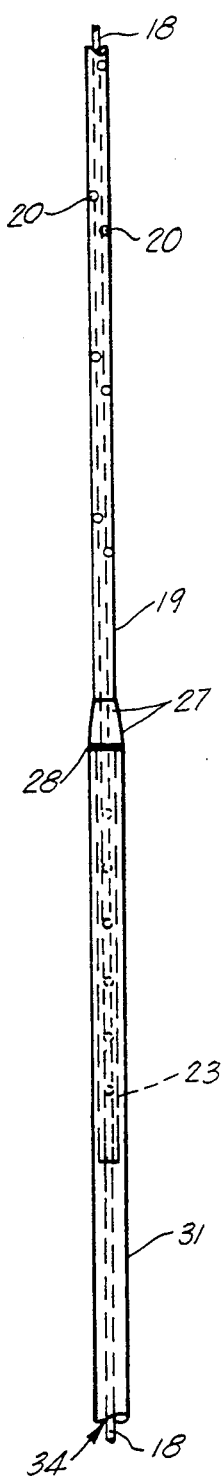
FIG. 9 is a schematic illustration of installation of the ureteral stent of the present invention using a larger pusher tube.

A pusher tube arrangement is used to force the tube body 19 further upwardly on the wire 18 until it is in the full operative position of FIG. 3. This pusher tube arrangement is shown in FIGS. 8 and 9. A dual pusher tube arrangement is used which includes a smaller diameter pusher tube 30 having an internal bore 33, and a larger diameter 31 pusher tube having a bore 34. It should be understood that the internal bore 33 of the smaller pusher tube 30 is large enough to accommodate the wire 18 as shown in FIG. 8. Additionally, it should be understood that the internal bore 34 of the larger pusher tube 31 is large enough to accommodate therewithin, as shown in FIGS. 8 and 9. In this fashion, the physician can use either of the pusher tubes 30, 31 as selected.

The installed configuration of ureteral stent apparatus 10 is shown in FIGS. 3 and 4. In FIG. 3, the upper or proximate end of the tube body 19 is placed in its operative position in the renal pelvis 12. This upper or proximate end 21 of the ureteral stent apparatus 10 is in the form of a double helix, as shown in FIGS. 5, 6 and 7. The double helix is also offset from the main tube body 19 as shown in FIGS. 5 and 6. In the end sectional view of FIG. 6, the bore 22 of tube body 19 is shown as extending from a side of the double helix. Thus, the main tube body 19 is laterally spaced from the center of the helical structure 21 as shown in FIG. 6. This offset configuration discourages migration of the ureteral stent 10 with respect to ureter 13. The double helix and its offset configuration registers tightly within the renal pelvis 12, as shown in FIG. 3.

The lower distal end of ureteral stent apparatus 10 is in the form of a bladder coil 23 that connects to the tube body 19 at hub 27. The hub 27 provides an internal bore that communicates with the bore 22 of tube body 19. The tube body 19 provides pores 20 spaced along its length as shown in FIG. 7. Similarly, the double helix structure 21 and the bladder coil structure 22 also provide small pores. The pores 29 are spaced along the bladder coil 23, as shown in FIG. 4. In FIG. 7, The proximate end 25 of the ureteral stent apparatus 10 is shown as defined by the double coil structure 21 and the distal or lower end portion of the ureteral stent apparatus 10 is shown as defined by bladder coil 23.

Hub or collar 27 provides an annular shoulder 28 that faces bladder coil 23. The annular shoulder 28 provides a load transfer surface that accepts an end of the larger diameter pusher tube 31. The larger diameter pusher tube is thus an outer pusher tube 31 as shown in FIGS. 8 and 9.

The inner pusher tube 30 is a smaller diameter pusher tube as shown in FIGS. 8 and 9. If placement of ureteral stent apparatus 10 is a simpler, less difficult placement, the physician simply uses the inner or smaller diameter pusher tube 30 and presses against the end 35 of bladder coil 23. If a more difficult placement is contemplated, the physician can use both inner pusher tube 30 and outer pusher tube 31. Both pusher tubes are placed against the distal end 26 of ureteral stent apparatus 10. This places the end of inner pusher tube 30 against the free end 35 of bladder coil 23 and the end of outer or larger diameter pusher tube 31 against annular shoulder 28 of collar 27. The physician can press on either or both of the pusher tubes 30, 31 in order to place the ureteral stent 10 in a desired position.

Ureteral stent apparatus 10 includes a tube body 19 of a harder durometer material and thus a stiffer material than the material of bladder coil 23. For example, both bladder coil 23 and tube body 19 can be of a commercially available polymer such as "C-Flex". However, the "C-Flex" material can be obtained in different durometer readings.

After placement of tube body 19 and double helix 21 in the position shown in FIGS. 3 and 4, the hub 28 is placed at ureteral orifice 16 as shown in FIG. 4. This is the desired position of ureteral stent apparatus 10, namely, the placement of double helix 21 at renal pelvis 12 and the placement of collar or hub 27 at ureteral orifice 16. The positions of double helix 12, tube body 19, collar 27, and bladder tube 23 can be confirmed using a fluoroscope. After visual confirmation of stent position and of proper placement of both the helical coil 21 and collar 27, the pushers 30 and 31 and wire 18 are removed. After removal, the small 30 and large 31 pusher tubes can be used as needed to ensure proper placement of collar 27 adjacent ureteral orifice, as shown in FIG. 4. After proper placement and removal of the pusher tubes 30, 31, the guide wire 18 is removed.

The following Parts List includes part numbers as used herein and in the drawings with corresponding part descriptions as used in the written specification.

| PARTS LIST | |
|---|---|
| Part Number | Description |
| 10 | ureteral stent apparatus |
| 11 | kidney |
| 12 | renal pelvis |
| 13 | ureter |
| 14 | lumen |
| 15 | bladder |
| 16 | ureteral orifice |
| 17 | cystoscope |
| 18 | wire |
| 19 | tube body |
| 20 | pores |
| 21 | double helix |
| 22 | tube body bore |
| 23 | bladder coil |
| 24 | bladder coil bore |
| 25 | proximal end portion |
| 26 | distal end portion |
| 27 | collar |
| 28 | annular shoulder |
| 29 | pores |
| 30 | inner pusher tube |
| 31 | outer pusher tube |
| 32 | arrow |
| 33 | bore |
| 34 | bore |

-continued

| PARTS LIST | |
|---|---|
| Part Number | Description |
| 35 | bladder coil free end |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A ureteral stent apparatus comprising:
 a) an elongated flexible tube body having a bore for carrying fluid with a central longitudinal bore axis, the tube body having proximal and distal end portions;
 b) the tube body including a double helical portion at the proximal end portion that is positioned during use at the patient's renal pelvis and wherein the center of the helical portion is laterally offset from the bore axis;
 c) a bladder coil positioned at the distal end portion of the tube body, and with a bore that communicates with the tube body bore;
 d) a hub that defines a connection between the softer bladder coil and the stiffer tube body, the hub having a greater diameter than the tube and bladder coil so that the hub can be used to place the tube body in a desired position in the urinary tract of a patient; and
 e) wherein the bladder coil is of a softer material than the tube body.

2. The stent of claim 1 wherein the tube is of a polymeric material.

3. The stent of claim 1 wherein the bladder coil is of a polymeric material.

4. The stent of claim 1 wherein the bladder coil is of a softer material than the tube body for reducing irritation of the trigone.

5. The stent of claim 1 wherein at least the hub is of a radiopaque material.

6. The stent of claim 1 wherein at least the tube body is of a radiopaque material.

7. The stent of claim 1 wherein the tube body has a hydrophilic coating.

8. The stent of claim 1 wherein the bladder coil forms a coil that defines a full circle.

9. The stent of claim 1 further comprising a wire placement member that fits the tube bore and wherein the tube body, bladder coil and double helical coil can be extended into an elongated straightened positioned for insertion of the tube body into the patients ureter when the wire member occupies the tube bore.

10. A ureteral stent apparatus comprising:
 a) an elongated flexible tube having a lumen for carrying fluid, the tube having a straight central portion, and proximal and distal end portions;
 b) the tube proximal end having a coiled portion that generates a circular path that is laterally offset from the straight tube portion, the proximal end portion being positioned during use at the patient's renal pelvis, for retention of the stent in a desired position;
 c) a bladder coil positioned at the distal end of the tube;
 d) a hub that defines a connection between the bladder coil and the tube, the hub having a diameter greater than the tube and bladder coil; and
 e) means for engaging the hub so that pressure can be applied to the hub for placing the hub into a selected position in the patient's urinary tract.

11. The stent of claim 10 wherein the tube is of a polymeric material.

12. The stent of claim 10 wherein the bladder coil is of a polymeric material.

13. The stent of claim 10 wherein the bladder coil is of a softer material than the tube body for reducing irritation of the trigone.

14. The stent of claim 10 wherein further comprising a collar positioned between the tube body and the bladder coil.

15. The stent of claim 14 wherein at least the hub is of a radiopaque material.

16. The stent of claim 10 wherein at least the tube body is of a radiopaque material.

17. The stent of claim 10 wherein the tube body has a hydrophilic coating.

18. The stent of claim 10 wherein the bladder coil forms a coil that defines a full circle.

19. The stent of claim 10 further comprising a wire placement member that fits the tube bore and wherein the tube body, bladder coil and double helical coil can be extended into an elongated straightened positioned for insertion of the tube body into the patients ureter when the wire member occupies the tube bore.

20. A ureteral stent apparatus comprising:
 a) an elongated flexible tube adapted for placement in a patient's ureter and having a lumen for carrying fluid between the patient's kidney and bladder, the tube having proximal and distal end portions;
 b) the tube proximal end portion having a helical portion that is positioned during use at the patient's renal pelvis;
 c) a bladder coil positioned at the distal end of the tube;
 d) a hub that defines a connection between the bladder coil and the tube, the hub having a diameter greater than the tube and bladder coil;
 e) a stiff guide member that is stiff enough to straighten the tube, bladder coil and helical portions during insertion into a patient's ureter;
 f) a pusher assembly including at least a member that can engage the hub so that pressure applied to the hub forces the tube body into a selected position in the ureter.

21. The apparatus of claim 20 wherein the pusher assembly includes a pair of tubular members including a larger and a smaller tubular member, each with a lumen, and one of the tubular members can fit within the lumen of the other tubular member.

22. The apparatus of claim 20 wherein the stiff guide member is of a radiopaque material.

23. The apparatus of claim 22 wherein the guide member is a metallic wire.

24. The apparatus of claim 21 wherein the larger tubular member can abut and engage the hub during a pushing of the stent during placement.

* * * * *